United States Patent [19]
Graiver et al.

[11] Patent Number: 5,481,014
[45] Date of Patent: Jan. 2, 1996

[54] SILYL PHOSPHONATE AS STABILIZING AGENT FOR POLYDIORGANOSILOXANES

[75] Inventors: Daniel Graiver; Eric J. Hough, both of Midland; Arnold W. Lomas, Rhodes, all of Mich.

[73] Assignee: Dow Corning Corporation, Midland, Mich.

[21] Appl. No.: 438,586

[22] Filed: May 8, 1995

[51] Int. Cl.$^6$ .................................................. C07F 7/08
[52] U.S. Cl. ............................................................. 556/401
[58] Field of Search ................................................ 556/401

[56] References Cited

U.S. PATENT DOCUMENTS

| | | | |
|---|---|---|---|
| 3,188,300 | 6/1965 | Chalk | 556/401 X |
| 4,177,200 | 12/1979 | Razzano et al. | 260/448.2 N |
| 4,460,726 | 7/1984 | Huber et al. | 556/401 X |
| 4,551,515 | 11/1985 | Herberg et al. | 528/18 |
| 4,683,319 | 7/1987 | Yoshitake et al. | 556/401 X |
| 5,041,586 | 8/1991 | Beck et al. | 556/405 |
| 5,099,051 | 3/1992 | Beck et al. | 556/401 |
| 5,274,154 | 12/1993 | Roth et al. | 556/401 |

*Primary Examiner*—Paul F. Shaver
*Attorney, Agent, or Firm*—William F. Boley

[57] ABSTRACT

A method for stabilizing a mixture comprising polydiorganosiloxane and an alkali metal. The method comprises contacting a silyl phosphonate described by formula $R^1_a(OH)_b(OSiR^2_3)_{3-a-b}P=O$, where each $R^1$ and $R^2$ is an independently selected hydrocarbyl radical comprising less than about twelve carbon atoms, a=1 or 2, b=0 or 1, and a+b=1 or 2, with a polydiorganosiloxane and an alkali metal.

17 Claims, No Drawings

SILYL PHOSPHONATE AS STABILIZING AGENT FOR POLYDIORGANOSILOXANES

BACKGROUND OF INVENTION

The present invention is a method for stabilizing a mixture comprising polydiorganosiloxane and an alkali metal. The method comprises contacting a silyl phosphonate described by formula $R^1_a(OH)_b(OSiR^2_3)_{3-a-b}P=O$, where each $R^1$ and $R^2$ is an independently selected hydrocarbyl radical comprising less than about twelve carbon atoms, a=1 or 2, b=0 or 1, and a+b=1 or 2, with a mixture comprising a polydiorganosiloxane and an alkali metal.

Polydiorganosiloxanes are used in the form of fluids and are crosslinked to form, for example, silicone rubbers and resins. Many of the uses of polydiorganosiloxanes fluids, silicone rubbers and resins require that the material be stable when exposed to high temperatures. Typically polydiorganosiloxanes are prepared by the process of heating low molecular weight linear polydiorganosiloxanes and cyclic polydiorganosiloxanes at a temperature above about 100° C. in the presence of a strong base such as potassium hydroxide or potassium silanolate to form an equilibrium mixture. Other known alkali metal catalyst for this type of polymerization include sodium hydroxide, cesium hydroxide, lithium hydroxide, and their corresponding silanolates or siloxanates. In the case of cyclic polydiorganosiloxane polymerization, a ring opening reaction occurs with the formation of linear polymers. Typically the product of this polymerization reaction is an equilibrium mixture comprising a linear polydiorganosiloxane as a major portion and cyclic polydiorganosiloxane as a minor portion. The presence of the cyclic polydiorganosiloxane in products is undesirable because it can have sufficiently high vapor pressure to cause problems during use, and therefore these cyclics are typically removed. The most convenient method of removing these cyclic siloxanes is by heating under reduced pressure. However if the basic caualyst's activity is not hindered additional cyclic siloxanes will be generated during the distillation process in an attempt to maintain equilibrium conditions. Therefore, it is important in the preparation of linear polydiorganosiloxanes to stabilize the basic catalyst to both improve yield of the process and to stabilize final products.

Various methods of stabilizing the basic catalysts which may be present in polydiorganosiloxanes have been used in the past. For example, strong acids such as hydrochloric acid and sulfuric acid have been suggested as useful. But since strong acids are also known equilibrium catalyst for cyclic and linear polydiorganosiloxanes, the amount of acid must be controlled carefully to prevent the presence of excess which can cause degradation of the polydiorganosiloxanes.

Triprotic acids such as phosphoric acid and arsenic acid have been proposed as useful for stabilizing basic catalysts comprising alkali metal compounds, since they can serve as a buffering agent. The use of arsenic acid is generally not desirable due to its toxicity. Although phosphoric acid has good buffering capability and low toxicity, its use as a neutralizing agent is limited due to its insolubility in polydiorganosiloxanes. To be an effective catalyst stabilizer the stabilizing material needs to be soluble in the polydiorganosiloxanes so that it can contact the alkali metal which is often located in the equilibrium mixture on the terminal silicon atoms of the polydiorganosiloxane.

Razzano et al., U.S. Pat. No. 4,177,200, describe a process for preparing silyl phosphates which are soluble in polydiorganosiloxanes. The silyl phosphates are prepared by the reaction of a linear siloxane and a phosphorous oxyhalogen or phosphoric acid. Razzano et al. teach the silyl phosphates are useful for the continuous neutralization of alkali metal hydroxides in an equilibrium mixture of polydiorganosiloxanes.

Petersen, U.S. Pat. No. 4,177,220, describes the use of a catalyst suitable for use in a process for preparing silyl phosphates. The process taught by Petersen comprises reacting phosphoric acid with a linear polysiloxane in the presence of a silyl phosphate. The presence of the silyl phosphate allows the reaction to initiate quickly and smoothly. A portion of the silyl phosphate from a previous run can be used as the catalytic amount of silyl phosphate. Petersen teaches the silyl phosphates prepared by the described process can be used as a neutralizing agent for neutralizing alkali metal hydroxides and bases in siloxane solutions.

Beck et al., U.S. Pat. No. 5,041,586, teach the preparation of silyl phosphate mixtures by adding phosphoric acid to hexamethyldisiloxane under reflux. The resulting mixture is report to comprise 10 to 30 weight percent of monosilyl phosphate, 65 to 85 weight percent of disilyl phosphate, and 2 to 7 weight percent of trisilyl phosphate. This mixture is reported to be useful in stabilizing basic polymerization catalyst such as potassium hydroxide or potassium silanolate, when such catalyst are present in polydiorganosiloxane mixtures.

Beck et al., U.S. Pat. No. 5,099,051, teach the preparation of siloxanyl-phosphate mixtures by reacting a cyclopolydimethylsiloxane and a silylphosphate mixture, as described in Beck et al., U.S. Pat. No. 5,041,586. The siloxanylphosphate mixtures are reported to be useful in stabilizing basic polymerization catalyst such as potassium hydroxide or potassium silanolate, when such catalyst are present in polydiorganosiloxane mixtures.

Herberg et al., U.S. Pat. No. 4,551,515, teach that agents such as phosphoric acid, tris(chloroethyl)phosphite and silyl phosphate can be use to neutralize basic polymerization catalyst present in compositions comprising polydiorganosiloxanes.

The present inventors have discovered that silyl phosphonates can be use to stabilize mixtures comprising polydiorganosiloxane and alkali metal. These silyl phosphonates are readily soluble in the polydiorganosiloxanes. Furthermore, and quite unexpectly the silyl phosphonates have a greatly improved shelf life diluted in cyclic polydiorganosiloxanes, in comparison to silyl phosphates diluted in cyclic polydiorganosiloxanes. This improved shelf life allows for a masterbatch dilution of the silyl phosphates to be made and used for an extended time in manufacturing processes. Another advantage of the present method is that in comparison to silyl phosphates which may contain residual phosphoric acid that can potentially form silicone gels, this potential does not exist with the silyl phosphonates.

SUMMARY OF INVENTION

The present invention is a method for stabilizing a mixture comprising polydiorganosiloxane and an alkali metal. The method comprises contacting a silyl phosphonate described by formula $R^1_a(OH)_b(OSiR^2_3)_{3-a-b}P=O$ where each $R^1$ and $R^2$ is an independently selected hydrocarbyl radical comprising less than about twelve carbon atoms, a=1 or 2, b=0 or 1, and a+b=1 or 2, with a polydiorganosiloxane and an alkali metal.

DESCRIPTION OF INVENTION

The present invention is a method for stabilizing polydiorganosiloxanes. The method comprises: contacting a mixture comprising a polydiorganosiloxane and an alkali metal with a stabilizing amount of a silyl phosphonate described by formula $R^1_a(OH)_b(OSiR^2_3)_{3-a-b}P=O$, where each $R^1$ and $R^2$ is an independently selected hydrocarbyl radical comprising less than about twelve carbon atoms, a=1 or 2, b=0 or 1, and a+b=1 or 2.

In the present method a stabilizing amount of a silyl phosphonate is contacted with a mixture comprising a polydiorganosiloxane and an alkali metal, thereby reducing the tendency of such a mixture to equilibrate to form a cyclic polydiorganosiloxane fraction. The polydiorganosiloxane which can be stabilized by the present process can be any of those known in the art. Generally, the polydiorganosiloxane can comprise repeating units described by formula —($R^3_2SiO)_x$—, where each $R^3$ can be an independently selected hydrocarbyl radical comprising less than about 12 carbon atoms. $R^3$ can be a saturated, unsaturated, substituted, or unsubstituted hydrocarbyl radical. $R^3$ can be for example, an alkyl such as methyl, ethyl, propyl, tert-butyl; an aryl such as phenyl; an alkenyl such as vinyl, allyl, hexenyl; a cycloalkyl such as cyclopentyl and cyclohexyl; a substituted alkyl such as 3,3,3-trifluoropropyl; and a substituted aryl such as chlorophenyl. The number of repeating units denoted by x is not limited and can be from about two to 100,000 or greater. The polydiorganosiloxane can be a linear or branched polymer. The polydiorganosiloxane can be monodispersed or polydispersed. The polydiorganosiloxane can be a homopolymer or a block or random copolymer. The polydiorganosiloxane may be end-terminated, for example, with silyl groups described by formula $R^3_2R^4SiO$—, where $R^3$ is as previously described and $R^4$ is selected from a group consisting of $R^3$, hydrogen, and hydroxy. The polydiorganosiloxane can be, for example, trimethylsilyl end-terminated polydimethylsiloxane, dimethylvinylsilyl end-terminated polydimethylsiloxane, dimethylvinylsilyl end-terminated polydimethylsiloxane having pendant vinyl groups attached to silicon, dimethylhydroxysilyl end-terminated polydimethylsiloxane, dimethylhydrosilyl end-terminated polydimethylsiloxane, dimethylhydrosilyl end-terminated polydimethylsiloxane having pendant hydrogens attached to silicon, trimethylsilyl or dimethyl(3,3,3-trifluoropropyl)silyl end-terminated polydiorganosiloxane having about 50 percent of pendant organic groups attached to silicon being methyl and the remainder being 3,3,3-trifluoropropyl, and trimethylsilyl end-terminated copolymer comprising methylphenylsiloxy and dimethylsiloxy units.

The present method is useful for stabilizing a mixture comprising a polydiorganosiloxane and an alkali metal, where the mixture results from the polymerization of cyclic or short-chain polydiorganosiloxanes, and mixtures thereof, in the presence of an alkali metal hydroxide or silanolate. Such a mixture can be made by polymerizing cyclic polydiorganosiloxane having on the average from three to six diorganosiloxy units per molecule with an alkali metal compound. The alkali metal compound can be metal hydroxides such as potassium hydroxide, sodium hydroxide, lithium hydroxide, cesium hydroxide, calcium hydroxide, and magnesium hydroxide or a metal silanolate derived from the same alkali metals. The present method is especially useful for stabilizing a mixture comprising polydimethylsiloxanes and potassium hydroxide or potassium silanolate.

The stabilizing agents useful in the present method are those silyl phosphonates and silyl phosphinates described by formula (1), both herein referred to as silyl phosphonate. By "stabilizing amount" it is meant that the silyl phosphonate is present at a concentration sufficient to reduce or prevent scission of the Si—O—Si bonds of the polydiorganosiloxane. The silyl phosphonate comprises one or two radicals $R^1$ bonded directly to the phosphorous atom. A preferred silyl phosphonate has one radical $R^1$ bonded directly to the phosphorous atom. Each $R^1$ can be an independently selected hydrocarbyl radical comprising less than about twelve carbon atoms. $R^1$ can be substituted, unsubstituted saturated, or unsaturated hydrocarbyl radicals. $R^1$ can be, for example, alkyl, alkenyl, aryl, and cycloalkyl. $R^1$ can be, for example, methyl, ethyl, butyl, vinyl, allyl, phenyl, cyclohexyl, and perfluoropropyl. Preferred is when $R^1$ is an unsubstituted hydrocarbyl radical comprising less than about seven carbon atoms. Even more preferred is when $R^1$ comprises about one to two carbon atoms. The silyl phosphonate can comprise one or two triorganosilyl radicals described by formula —$SiR^2_3$, where each $R^2$ is an independently selected hydrocarbyl radical comprising less than about twelve carbon atoms. $R^2$ can be substituted, unsubstituted, saturated, or unsaturated hydrocarbyl radicals. $R^2$ can be, for example, alkyl, alkenyl, aryl, and cycloalkyl. $R^2$ can be, for example, methyl, ethyl, butyl, vinyl, allyl, phenyl, cyclohexyl, and perfluoropropyl. Preferred is when $R^2$ is methyl. The silyl phosphonate can be, for example, bis(trimethylsilyl) vinyl phosphonate, trimethylsilyl vinyl phosphonate, bis(trimethylsilyl) propyl phosphonate, bis(trimethylsilyl) phenyl phosphonate, bis(trimethylsilyl) benzyl phosphonate, trimethylsilyl divinyl phosphinate, bis(trimethylsilyl) methyl phosphinate, trimethylsilyl dimethyl phosphinate, trimethylsilyl methyl phenyl phosphinate, trimethylsilyl diphenyl phosphinate, and triphenylsilyl diphenyl phosphinate. The silyl phosphonate can be a mixture of mono and bis(triorganosilyl) phosphonates.

The method for preparing the silyl phosphonate is not critical to the present invention and can be any of those known in the art. For example, reference to such preparatory procedures is made in Tetrahedron, Vol. 45, No. 9, p. 2479, where it is taught that silyl esters of P=O acids can be obtained by silylation of the acid with alkoxysilanes, triorganosilanols, or disiloxanes. A preferred method for making the silyl phosphonate is provided in Example 1 herein.

The silyl phosphonate described by formula (1) is highly soluble in polydiorganosiloxanes and therefore quickly intermixes with the mixture comprising a polydiorganosiloxane and an alkali metal to neutralize the alkali metal. Furthermore, the silyl phosphonate acts as a buffering type of neutralizing agent, that is, exact amounts do not have to be metered into the mixture to obtain an exact neutralization of the alkali metal. The buffering capacity of the silyl phosphonate prevents the formation of excess acidity in the stabilized mixture and avoids the necessity for back neutralization. Because of the buffering type activity of the silyl phosphonate the stabilizing amount of silyl phosphonate can be any amount which reduces scission of Si—O—Si bonds in the polydiorganosiloxane polymer to an excess of that required to reduce or prevent such scission. Generally it is preferred to provide at least a stoichiometric excess of the silyl phosphonate relative to the alkali metal atoms present in the polydiorganosiloxane. More preferred is at least one phosphorous atom per 1.5 alkali metal atoms.

Because of the small amount of silyl phosphonate typically required to stabilize a mixture comprising the polydiorganosiloxane and alkali metal, it may be desirable to dilute the silyl phosphonate in a diluent. Such dilution can facilitate the delivery of accurate amounts of the silyl phosphonate to the present method. In a preferred process the silyl phosphonate is diluted in a cyclic polydiorganosiloxane such as octamethyltetracyclosiloxane or a mixture of cyclic polydiorganosiloxanes. The present inventors have found that silyl phosphonates described by formula (1) can have increased storage stability diluted in cyclic polydiorganosiloxanes, when compared to similarly diluted silyl phosphate.

The method for contacting the mixture comprising the polydiorganosiloxane and alkali metal with the silyl phosphonate can be any standard method, for example, a mixer, blender, mill, reactor, or the like. The temperature at which the mixture comprising the polydiorganosiloxane and alkali metal is contacted with the silyl phosphonate is not critical and can generally be any temperature above about 20° C. A preferred temperature is within a range of about 100° C. to 300° C. Even more preferred is a temperature within a range of about 225° C. to 275° C. The present method for stabilizing polydiorganosiloxanes can be conducted as a batch process or as a continuous process. In some cases it may be desirable to first stabilize the polydiorganosiloxanes with $CO_2$ and then add the silyl phosphonate to neutralize residual alkali metal not neutralized by the $CO_2$.

The following examples are provided to illustrate the present invention. These examples are not intended to limit the scope of the provided claims.

EXAMPLE 1

The ability of bis(trimethylsilyl) vinyl phosphonate to stabilize a polydimethylsiloxane gum was evaluated. The bis(trimethylsilyl) vinyl phosphonate was prepared by adding 0.33 mole of vinyl phosphonic acid and 0.46 mole of hexamethyldisiloxane (HMDS) to a 250 mL flask. The flask was purged with dry nitrogen and maintained under a nitrogen blanket during conduct of the process. The reaction mixture was heated to its reflux temperature of about 92° C. to 96° C. and water was removed from the flask by azeotropic distillation using the excess HMDS as the azeotropic solvent. After five hours of refluxing, the temperature of the flask content was 110° C. Refluxing was continued for an additional 1.6 hours, at the end of which time the temperature was 112° C. The flask was then cooled to 25° C. and a clear amber liquid product recovered. Excess HMDS was stripped from the product by distilling at 55° C., for 0.5 hour, at 10 mm Hg pressure. The stripped product was analyzed by gas chromatography using a mass spectrometer detector (GC/MS), $p^{131}$ nuclear magnetic resonance (NMR), and fourier transform infrared spectrometer (FTIR) and determined to be an equilibrium mixture comprising primarily bis(trimethylsilyl) vinyl phosphonate with a minor mono(trimethylsilyl) vinyl phosphonate component.

One gram of the bis(trimethylsilyl)vinyl phosphonate prepared as described above was added to 49 grams of octamethyltetracyclosiloxane (D4). A mixer was then loaded with 1 kg of a $CO_2$ neutralized dimethylvinyl end-terminated polydimethylsiloxane gum having 0.14 mole percent pendent vinyl (Williams plasticity 140–165 mm/100 s) which contained 18–20 ppm potassium. About 2.8 g of the mixture comprising bis(trimethylsilyl) vinyl phosphonate in D4 was then added to the mixer. The mixer was sealed and run at 35 rpm under $N_2$ at a temperature of 250° C., at 20 mm Hg, for about 0.5 to one hour. For comparison, a trimethylsilyl phosphate mixture as described in U.S. Pat. No. 5,041,586 was diluted about 1:40 in D4 and evaluated. A similar 1 kg sample of siloxane gum was neutralized with this mixture at a 2.5:1 mole ratio of potassium to phosphorous by the same process used with the silyl phosphonate.

The heat stability of the treated dimethylvinyl end-terminated polydimethylsiloxane gum was determined by standard thermalgravimetric procedures. The unstabilized gum exhibited a 10% weight loss at 310° C. The material stabilized with tri(trimethylsilyl) phosphate exhibited a 10% weight loss at 450° C. The material stabilized with bis(trimethylsilyl) vinyl phosphonate exhibited a 10% weight loss at 450° C.

EXAMPLE 2

The stability of various bis(trimethylsilyl) organo phosphonates in octamethyltetracyclosiloxane (D4) was evaluated. The bis(trimethylsilyl) organo phosphonates were prepared by a method similar to that described in Example 1. The mixture comprising the bis(trimethylsilyl) organo phosphonates was analyzed by the procedures described in Example 1 and determined to be an equilibrium mixture comprising primarily the bis(trimethylsilyl) organo phosphonate with a minor mono(trimethylsilyl) organo phosphonate fraction. The organic substituent bonded to phosphorous is described in Table 1 under the heading "$R^1$". The mixture comprising the bis(trimethylsilyl) organo phosphonate was diluted in D4 at a concentration of 0.4 g phosphorous per 1 ml. For comparison purposes, a silyl phosphate mixture similar to that described in Example 1 was diluted in D4 at a concentration of 0.3 g phosphorous per 1 ml. The diluted mixtures were stored in sealed glass ampules at 55° C. At the times indicated in Table 1, the content of an ampule was analyzed for viscosity using a Brookfield viscometer. The results are reported in Table 1 in centipoise (cP).

TABLE 1

Stability of Bis (trimethylsilyl) Organo Phosphonate in D4

| $R^1$ | Viscosity (cP) | | | | |
|---|---|---|---|---|---|
| | 0 Day | 10 Day | 32 Day | 65 Day | 94 Day |
| propyl | 4 | 212 | 389 | 367 | 411 |
| phenyl | 4 | 169 | 180 | 164 | 173 |
| benzyl | 4 | 190 | 192 | 183 | 179 |
| vinyl | 4 | 191 | 183 | 166 | 176 |
| None (Silyl Phosphate) | 4 | 428 | 698 | 753 | 785 |

We claim:

1. A method for stabilizing polydiorganosiloxanes, the method comprising: contacting a mixture comprising a polydiorganosiloxane and an alkali metal with a stabilizing amount of a silyl phosphonate described by formula $$R^1_a(OH)_b(OSiR^2_3)_{3-a-b}P{=}O,$$

where each $R^1$ and $R^2$ is an independently selected hydrocarbyl radical comprising less than about twelve carbon atoms, a=1 or 2, b=0 or 1, and a+b=1 or 2.

2. A method according to claim 1, where the polydiorganosiloxane is selected from a group consisting of trimethylsilyl end-terminated polydimethylsiloxane, dimethylvinylsilyl end-terminated polydimethylsiloxane, dimethylvinylsilyl end-terminated polydimethylsiloxane having pendant vinyl groups attached to silicon, dimethylhydroxysilyl end-terminated polydimethylsiloxane, dimethylhydrosilyl end-terminated polydimethylsiloxane, dimethylhydrosilyl end-terminated polydimethylsiloxane having pendant hydrogens attached to silicon, and trimethylsilyl and dimethyl(3,3,3-trifluoropropyl)silyl end-terminated polydiorganosiloxane having about 50 percent of pendant organic groups attached to silicon being methyl and the remainder being 3,3,3-trifluoropropyl.

3. A method according to claim 1, where the alkali metal is potassium.

4. A method according to claim 1, where a=1.

5. A method according to claim 1, where $R^1$ is an unsubstituted hydrocarbyl radical comprising less than about seven carbon atoms.

6. A method according to claim 1, where $R^1$ comprises about one to two carbon atoms.

7. A method according to claim 1, where $R^1$ is vinyl.

8. A method according to claim 1, where $R^2$ is methyl.

9. A method according to claim 1, where the silyl phosphonate is selected from a group consisting of bis(trimethylsilyl) vinyl phosphonate, trimethylsilyl vinyl phosphonate, bis(trimethylsilyl) propyl phosphonate, bis(trimethylsilyl) phenyl phosphonate, bis(trimethylsilyl) benzyl phosphonate, trimethylsilyl divinyl phosphinate, bis(trimethylsilyl) methyl phosphonate, trimethylsilyl dimethyl phosphinate, trimethylsilyl methyl phenyl phosphinate, trimethylsilyl diphenyl phosphinate, and triphenylsilyl diphenyl phosphinate.

10. A method according to claim 1, where the silyl phosphonate is a mixture of mono and bis(triorganosilyl) phosphonates.

11. A method according to claim 1, where the silyl phosphonate is present in least a stoichiometric excess relative to the alkali metal present in the mixture.

12. A method according to claim 1, where the silyl phosphonate provides at least one phosphorous atom per 1.5 alkali metal atom present in the mixture.

13. A method according to claim 1, where the silyl phosphonate is diluted in a cyclic polydiorganosiloxane prior to contact with the mixture.

14. A method according to claim 1, where the mixture is contacted with the silyl phosphonate at a temperature within a range of about 100° C. to 300° C.

15. A method according to claim 1, where the mixture is contacted with the silyl phosphonate at a temperature within a range of about 225° C. to 275° C.

16. A method according to claim 1, where the mixture is stabilized with carbon dioxide gas before contact with the silyl phosphonate.

17. A method according to claim 1, where the polydiorganosiloxane is dimethylvinylsilyl end-terminated polydimethylsiloxane having pendant vinyl groups attached to silicon, the alkali metal is potassium, the silyl phosphonate is selected from a group consisting of trimethylsilyl vinyl phosphonate and bis(trimethylsilyl) vinyl phosphonate, the silyl phosphonate is diluted in a cyclic polydiorganosiloxane prior to contact with the mixture, the silyl phosphonate is present in at least stoichiometric excess relative to the potassium, and the silyl phosphonate is contacted with the mixture at a temperature within a range of about 225° C. to 275° C.

* * * * *